(12) United States Patent
Müller et al.

(10) Patent No.: US 6,544,931 B1
(45) Date of Patent: Apr. 8, 2003

(54) SUBSTITUTED HETEROARYLOXYACETANILIDES AND THEIR USE AS HERBICIDES

(75) Inventors: Klaus-Helmut Müller, Düsseldorf (DE); Lothar Rohe, Wuppertal (DE); Joachim Kluth, Langenfeld (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/031,174

(22) PCT Filed: Jul. 7, 2000

(86) PCT No.: PCT/EP00/06461

§ 371 (c)(1),
(2), (4) Date: Jan. 16, 2002

(87) PCT Pub. No.: WO01/05777

PCT Pub. Date: Jan. 25, 2001

(30) Foreign Application Priority Data

Jul. 20, 1999 (DE) .......................... 199 33 936

(51) Int. Cl.⁷ ...................... C07D 285/13; A01N 43/74
(52) U.S. Cl. ...................... 504/262; 504/263; 504/265; 504/267; 504/270; 548/129; 548/132; 548/137; 548/165; 548/182; 548/183; 548/186; 548/187; 548/221; 548/229
(58) Field of Search ................... 548/165, 151, 548/186, 129, 182, 183, 187; 518/132, 137, 221, 229; 564/270, 267, 265, 262, 263

(56) References Cited

U.S. PATENT DOCUMENTS

| | | |
|---|---|---|
| 4,509,971 A | 4/1985 | Förster et al. .................. 71/90 |
| 4,585,471 A | 4/1986 | Förster et al. .................. 71/90 |
| 4,645,525 A | 2/1987 | Förster et al. .................. 71/88 |
| 4,708,731 A | 11/1987 | Förster et al. .................. 71/90 |
| 4,968,342 A | 11/1990 | Förster et al. .................. 71/90 |
| 4,988,380 A | 1/1991 | Förster et al. .................. 71/90 |
| 5,090,991 A | 2/1992 | Förster et al. .................. 71/90 |

FOREIGN PATENT DOCUMENTS

| | | |
|---|---|---|
| DE | 22 01 432 | 7/1973 |
| DE | 30 38 608 | 5/1982 |
| EP | 5 501 | 11/1979 |
| EP | 10 673 | 5/1980 |
| EP | 18 497 | 11/1980 |
| EP | 0 37 524 | 10/1981 |
| EP | 0 037 526 | 10/1981 |
| EP | 0 037 527 | 10/1981 |
| EP | 94 541 | 11/1983 |
| EP | 100 044 | 2/1984 |

*Primary Examiner*—Robert Gerstl
(74) *Attorney, Agent, or Firm*—Richard E. L. Henderson; John E. Mrozinski, Jr.

(57) ABSTRACT

The invention relates to novel substituted heteroaryloxyacetanilides of the general formula (I),

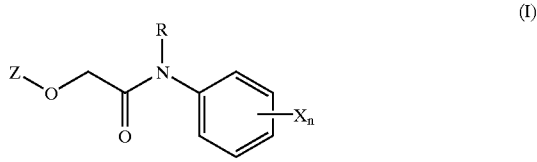

in which n, R, X, and Z are to intermediates for their preparation and to their use as herbicides.

8 Claims, No Drawings

SUBSTITUTED HETEROARYLOXYACETANILIDES AND THEIR USE AS HERBICIDES

FIELD OF THE INVENTION

This application is a 371 of PCT/EP00/06461 filed Jul. 7, 2000.

The invention relates to novel substituted heteroaryloxyacetanilides, to a process and to intermediates for their preparation and to their use as herbicides.

BACKGROUND OF THE INVENTION

It is already known that certain substituted heteroaryloxyacetanilides have herbicidal properties (cf. EP-A-037524, cf. also EP-A-005501, EP-A-18497, EP-A-37526, EP-A-37527, EP-A-94541, EP-A-100044, EP-A-148501, EP-A-300344, EP-A-348734, EP-A-348737, U.S. Pat. No. 4,509,971, U.S. Pat. No. 4,585,471, U.S. Pat. No. 4,645,525, U.S. Pat. No. 4,708,731, U.S. Pat. No. 4,968,342, and U.S. Pat. No. 4,988,380). However, the activity of these prior-art compounds is, in particular at low application rates and concentrations, not entirely satisfactory in all areas of use.

SUMMARY OF THE INVENTION

A substituted heteroaryloxyacetanilide of the general formula I

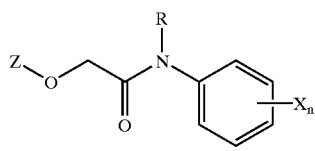

(I)

which has herbicidal activity.

DETAILED DESCRIPTION OF THE INVENTION

This invention, accordingly, provides novel substituted heteroaryloxyacetanilides of the general formula (I)

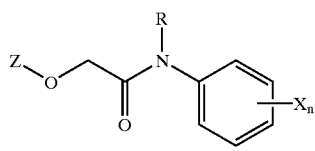

(I)

in which n represents the number 0, 1, 2 or 3,

R represents s-butyl, t-butyl, 1-ethyl-propyl, 2-propinyl, 1-methyl-2-propinyl, 1-ethyl-2-propinyl, 2-butinyl, 1-methyl-2-butinyl or 1-ethyl-2-butinyl, X represents nitro, cyano, fluorine, chlorine, bromine or represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethyl sulphinyl, n- or i-propylsulphinyl, methylsulphonyl, ethylsulphonyl, n- or i-propylsulphonyl, and Z represents heteroaryl from the group consisting of oxazolyl, benzoxazolyl, thiazolyl, benzothiazolyl, oxadiazolyl, thiadiazolyl, each of which is optionally substituted by nitro, cyano, carbamoyl, thiocarbamoyl, fluorine, chlorine, bromine, or by (in each case optionally cyano-, fluorine-, chlorine-, methoxy- or ethoxy-substituted) methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl.

Preferred substituents or ranges of the radicals present in the formulae mentioned above and below are described below.

n preferably represents the number 0, 1 or 2.

R preferably represents s-butyl, t-butyl, 1-ethyl-propyl, 2-propinyl or 1-methyl-2-propinyl.

X preferably represents nitro, cyano, fluorine, chlorine, bromine or represents in each case optionally cyano-, fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl or ethylsulphonyl.

Z preferably represents heteroaryl from the group consisting of oxazolyl, benzoxazolyl, thiazolyl, benzothiazolyl, 1,2,4-oxadiazolyl, 1,3,4-oxadiazolyl, 1,2,4-thiadiazolyl, 1,3,4-thiadiazolyl, each of which is optionally substituted by nitro, cyano, carbamoyl, thiocarbamoyl, fluorine, chlorine, bromine, or by (in each case optionally cyano-, fluorine-, chlorine-, methoxy- or ethoxy-substituted) methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

n particularly preferably represents the number 0, 1 or 2.

R particularly preferably represents s-butyl, t-butyl, 1-ethyl-propyl, 2-propinyl or 1-methyl-2-propinyl.

X particularly preferably represents nitro, cyano, fluorine, chlorine, bromine or represents in each case optionally fluorine- and/or chlorine-substituted methyl, ethyl, n- or i-propyl, methoxy, ethoxy, methylthio, ethylthio, methylsulphinyl, ethylsulphinyl, methylsulphonyl or ethylsulphonyl.

Z particularly preferably represents heteroaryl from the group consisting of oxazolyl, benzoxazolyl, thiazolyl, benzothiazolyl, 1,2,4-oxadiazolyl, 1,2,4-thiadiazolyl, 1,3,4-thiadiazolyl, each of which is optionally substituted by nitro, cyano, carbamoyl, thiocarbamoyl, fluorine, chlorine, bromine, or by (in each case optionally fluorine- and/or chlorine-substituted) methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

n very particularly preferably represents the number 0 or 1.

R very particularly preferably represents t-butyl, 1-ethyl-propyl or 2-propinyl.

X very particularly preferably represents cyano, fluorine, chlorine, methyl, ethyl, trifluoromethyl, methoxy or trifluoromethoxy.

Z very particularly preferably represents heteroaryl from the group consisting of oxazolyl, benzoxazolyl, thiazolyl, benzothiazolyl, 1,2,4-oxadiazolyl, 1,2,4-thiadiazolyl, 1,3,4-thiadiazolyl, each of which is optionally substituted by nitro, fluorine, chlorine, bromine, methyl, ethyl, n- or i-propyl, difluoromethyl, trifluoromethyl, difluorochloromethyl, fluorodichloromethyl, dichloromethyl, trichloromethyl, methylthio, ethylthio, n- or i-propylthio.

The abovementioned general or preferred radical definitions apply both to the end products of the formula (I) and correspondingly to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings given above as being preferred.

Particular preference according to the invention is given to those compounds of the formula (I) which contain a combination of the meanings given above as being particularly preferred.

Very particular preference according to the invention is given to those compounds of the formula (I) which contain a combination of the meanings given above as being very particularly preferred.

Optionally substituted radicals can be mono- or polysubstituted, where in the case of polysubstitution the substituents can be identical or different.

A very particularly preferred group are those compounds of the formula (I) in which n represents the number 0 or 1, R represents t-butyl, X represents cyano, fluorine, chlorine, methyl, ethyl, trifluoromethyl, methoxy or trifluoromethoxy, and Z represents heteroaryl from the group consisting of oxazolyl, benzoxazolyl, thiazolyl, benzothiazolyl, 1,2,4-thiadiazolyl, 1,3,4-thiadiazolyl, each of which is optionally substituted by fluorine, chlorine, bromine, methyl, ethyl, difluoromethyl, trifluoromethyl, dichloromethyl or trichloromethyl.

A further very particularly preferred group are those compounds of the formula (I) in which n represents the number 0 or 1, R represents 2-propinyl, X represents cyano, fluorine, chlorine, methyl, ethyl, trifluoromethyl, methoxy or trifluoromethoxy, and Z represents heteroaryl from the group consisting of oxazolyl, benzoxazolyl, thiazolyl, benzothiazolyl, 1,2,4-thiadiazolyl, 1,3,4-thiadiazolyl, each of which is optionally substituted by fluorine, chlorine, bromine, methyl, ethyl, difluoromethyl, trifluoromethyl, dichloromethyl or trichloromethyl.

The novel substituted heteroaryloxyacetanilides of the general formula (I) have interesting biological properties. In particular, they have strong and selective herbicidal activity.

The novel substituted heteroaryloxyacetanilides of the general formula (I) are obtained when heteroarenes of the general formula (II)

Z—X¹ (II)

in which

Z is as defined above and

X¹ represents fluorine, chlorine, bromine, methylthio, methylsulphinyl or methylsulphonyl, are reacted with hydroxyacetanilides of the general formula (III)

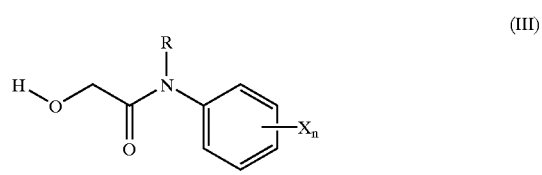

in which n, R and X are each as defined above, if appropriate in the presence of an acid binder and if appropriate in the presence of a diluent.

Using, for example, 2-chloro-benzoxazole and N-(t-butyl)-N-(3-fluoro-phenyl)-2-hydroxyacetamide as starting materials, the course of the reaction in the process according to the invention can be illustrated by the following reaction scheme:

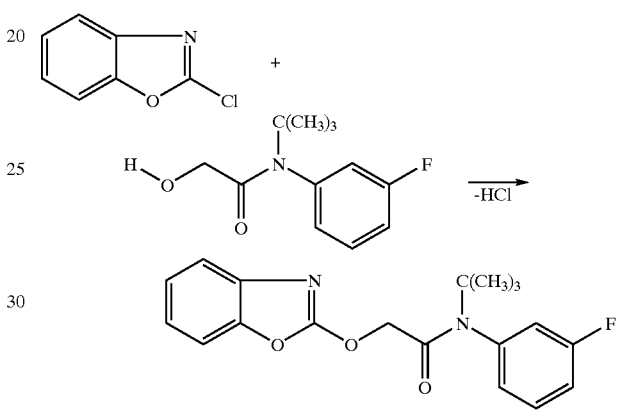

The formula (II) provides a general definition of the heteroarenes to be used as starting materials in the process according to the invention for preparing compounds of the general formula (I). In the general formula (II), Z preferably or in particular has that meaning which has already been mentioned above, in connection with the description of the compounds of the general formula (I) according to the invention, as being preferred or as being particularly preferred for Z; X¹ preferably represents chlorine or methylsulphonyl.

The starting materials of the general formula (II) are known organic chemicals for synthesis.

The formula (III) provides a general definition of the hydroxyacetanilides further to be used as starting materials in the process according to the invention for preparing compounds of the general formula (I). In the general formula (III), n, R and X each preferably or in particular have those meanings which have already been mentioned above, in connection with the description of the compounds of the general formula (I) according to the invention, as being preferred or as being particularly preferred for n, R and X.

The starting materials of the general formula (III), except for the compounds N-(s-butyl)-N-(4-ethoxy-phenyl)-2-hydroxyacetamide, N-(s-butyl)-N-(4-methyl-phenyl)-2-hydroxyacetamide, N-(t-butyl)-N-phenyl-2-hydroxyacetamide, N-phenyl-N-(2-propinyl)-2-hydroxyacetamide and N-phenyl-N-(1-methyl-2-propinyl)-2-hydroxyacetamide (cf. DE-A-2160380, DE-A-2201432, DE-A-3038608, EP-A-753507, U.S. Pat. No. 3954827), have not yet been disclosed in the literature. Except for the compounds N-(s-butyl)-N-(4-ethoxy-phenyl)-2-hydroxyacetamide, N-(s-butyl)-N-(4-methylphenyl)-2- hydroxyacetamide, N-(t-butyl)-N-phenyl-2-hydroxyacetamide, N-phenyl-N-(2-propinyl)-2-hydroxyacetamide and N-phenyl-N-(1-methyl-2-propinyl)-2-hydroxyacetamide, they also form, as novel substances, part of the subject-matter of the present application.

The hydroxyacetanilides of the general formula (III) are obtained when halogenoacetanilides of the general formula (IV)

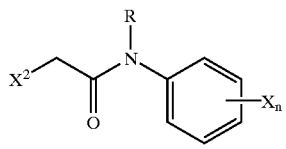

(IV)

in which n, R and X are each as defined above and $X^2$ represents fluorine, chlorine or bromine (in particular chlorine)

are reacted with alkali metal acetates, such as, for example, sodium acetate or potassium acetate, if appropriate in the presence of reaction auxiliaries, such as, for example, potassium carbonate and triethylamine, and if appropriate in the presence of diluents, such as, for example, N,N-dimethylformamide or N,N-dimethyl-acetamide, at temperatures between 50° C. and 150° C., and the resulting acetoxyacetanilides of the general formula (V)

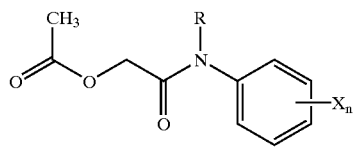

(V)

in which n, R and X are each as defined above are—if appropriate after intermediate isolation or else "in situ"—reacted with methanol, if appropriate in the presence of an acid acceptor, such as, for example, sodium methoxide, at temperatures between 20° C. and 100° C., and worked up by customary methods (cf. the Preparation Examples).

The halogenoacetanilides of the general formula (IV) required as precursors are known and/or can be prepared by processes known per se (cf. DE-A-2362743, DE-A-2633159, U.S. Pat. No. 3345151).

The halogenoacetanilides of the general formula (IV) are obtained when N-substituted anilines of the general formula (VI)

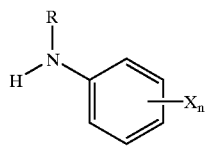

(VI)

in which n, R and X are each as defined above are reacted with halogenoacetyl halides of the general formula (VII)

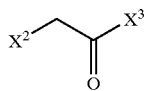

(VII)

in which $X^2$ and $X^3$ each represent fluorine, chlorine or bromine (in particular chlorine), if appropriate in the presence of a reaction auxiliary, such as, for example, pyridine, and if appropriate in the presence of a diluent, such as, for example, toluene, at temperatures between 0° C. and 100° C. (cf. the Preparation Examples).

Suitable diluents for carrying out the process according to the invention for preparing the compounds of the general formula (I) are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable acid binders for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethyl-aniline, N,N-dimethyl-benzylamine, pyridine, 2-methyl-, 3-methyl-. 4-methyl-, 2,4-dimethyl-, 2,6-dimethyl-, 3,4-di-methyl- and 3,5-dimethyl-pyridine, 5-ethyl-2-methyl-pyridine, 4-dimethylamino-pyridine, N-methyl-piperidine, 1.4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

When carrying out the process according to the invention, the reaction temperatures can be varied within a relatively wide range. In general, the process is carried out at temperatures between −20° C. and 100° C., preferably between 0° C. and 60° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible for one of the components to be used in a relatively large excess. The reaction Is generally carried out in a suitable diluent in the presence of an acid binder, and the reaction mixture is generally stirred at the required temperature for several hours. Work-up is carried out by customary methods (cf. the Preparation Examples).

The active compounds according to the invention can be used as defoliants, desiccants, haulm killers and, especially, as weedkillers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, lpomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

Depending on the concentration, the active compounds according to the invention are suitable for total weed control, for example on industrial terrain and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclone, benzofenap, benzoylprop(-ethyl), bialaphos. bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazone, chlorimuron(-ethyl), chlornitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop(-P-ethyl), fentrazamide, flamprop (-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate-(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-) metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxnim, pyributicarb, pyridate, pyriminobac(-methyl), pyrithiobac(-sodium), quinchlorac, quinmerac, quinoclamine, quizalofop (-P-ethyl), quizalofop(-P-tefuryl), nrmsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

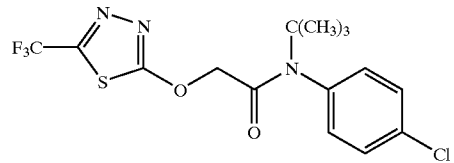

A mixture of 5.0 g (21 mmol) of N-(t-butyl)-N-(4-chlorophenyl)-2-hydroxyacetamide, 4.9 g (21 mmol) of 2-methylsulphonyl-5-trifluoromethyl-1,3,4-thiadiazole and 50 ml of acetone is cooled to −15° C. and, at this temperature, admixed dropwise with stirring with a solution of 1.4 g (35 mmol) of sodium hydroxide in 7 ml of water. The reaction mixture is stirred at −15° C. for 3 hours, then adjusted to pH 5 using acetic acid and subsequently poured into 500 ml of ice-water. The solvent is decanted off and the oily product that remains is crystallized by digestion with petroleum ether and then isolated by filtration with suction.

This gives 6.5 g (79% of theory) of N-(t-butyl)-N-(4-chlorophenyl)-2-(5-trifluoromethyl-1,3,4-thiadiazol-2-yl-oxy)-acetamide of melting point 82° C.

Example 2

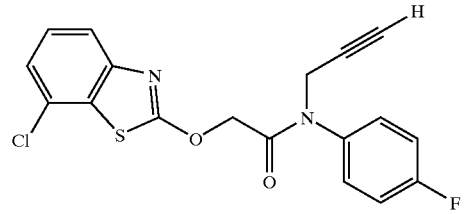

At room temperature (about 20° C.), 2.1 g (10 mmol) of 2,6-dichloro-benzothiazole are added with stirring to a mixture of 2.1 g (10 mmol) of N-(4-fluorophenyl)-N-(2-propinyl)-2-hydroxyacetamide, 0.15 g (12.5 mmol) of sodium hydroxide, 2 ml of water and 30 ml of acetone, and the reaction mixture is stirred at room temperature for 15 hours. The mixture is then shaken thoroughly with 150 ml of methylene chloride and the organic phase is separated off, washed with water, dried with sodium sulphate and filtered. The filtrate is concentrated under waterpump vacuum, the residue is digested with diisopropyl ether and the crystalline product is isolated by filtration with suction.

This gives 2.0 g (97% of theory) of N-(4-fluorophenyl)-N-(2-propinyl)-2-(6-chlorobenzothiazol-2-yl-oxy)-acetamide of melting point 126° C.

Analogously to Examples 1 and 2, and in accordance with the general description of the preparation process according to the invention, it is also possible to prepare, for example, the compounds of the general formula (I) listed in Table 1 below.

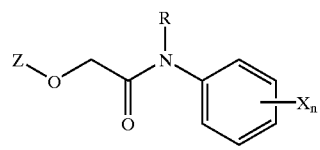

(I)

TABLE 1

Examples of compounds of the formula (I)

| Ex. No. | R | (aryl with $X_n$) | Z | Physical data |
|---|---|---|---|---|
| 3 | –CH₂–C≡C–CH₃ (but-2-ynyl) | 3-CF₃-phenyl | 5-CF₃-2-methyl-1,3,4-thiadiazol-2-yl | logP = 3.45[a] |
| 4 | –CH₂–C≡C–CH₃ (but-2-ynyl) | 4-F-phenyl | 5-CF₃-2-methyl-1,3,4-thiadiazol-2-yl | logP = 2.97[a] |
| 5 | –CH₂–C≡CH (2-propinyl) | 4-F-phenyl | 6-chlorobenzothiazol-2-yl | m.p.: 116° C. |
| 6 | –CH₂–C≡CH (2-propinyl) | 4-F-phenyl | benzoxazol-2-yl | m.p.: 138° C. |
| 7 | C(CH₃)₃ | 4-F-phenyl | 5-CF₃-2-methyl-1,3,4-thiadiazol-2-yl | m.p: 85° C. |
| 8 | C(CH₃)₃ | 3-F-phenyl | 5-CF₃-2-methyl-1,3,4-thiadiazol-2-yl | m.p.: 98° C. |
| 9 | C(CH₃)₃ | 3-Cl-phenyl | 5-CF₃-2-methyl-1,3,4-thiadiazol-2-yl | m.p.: 84° C. |
| 10 | C(CH₃)₃ | phenyl | 5-CF₃-2-methyl-1,3,4-thiadiazol-2-yl | m.p.: 86° C. |

TABLE 1-continued

Examples of compounds of the formula (I)

| Ex. No. | R | (aryl-X$_n$) | Z | Physical data |
|---|---|---|---|---|
| 11 | C(CH$_3$)$_3$ | 2-F-phenyl | 2-CF$_3$-5-methyl-1,3,4-thiadiazole | m.p.: 100° C. |
| 12 | C(CH$_3$)$_3$ | 2-Cl-phenyl | 2-CF$_3$-5-methyl-1,3,4-thiadiazole | m.p.: 77° C. |
| 13 | CH$_3$CH$_2$-C≡C-H | 4-C$_2$H$_5$-phenyl | 2-methyl-benzoxazole | |
| 14 | CH$_3$CH$_2$-C≡C-H | 4-Cl-phenyl | 2-methyl-benzoxazole | |
| 15 | C(CH$_3$)$_3$ | 4-C$_2$H$_5$-phenyl | 2-methyl-benzoxazole | |
| 16 | C(CH$_3$)$_3$ | 4-Cl-phenyl | 2-methyl-benzoxazole | |
| 17 | C(CH$_3$)$_3$ | 4-F-phenyl | 2-methyl-benzoxazole | |
| 18 | C(CH$_3$)$_3$ | 4-CF$_3$-phenyl | 2-CF$_3$-5-methyl-1,3,4-thiadiazole | |
| 19 | C(CH$_3$)$_3$ | 4-F-phenyl | 2-CF$_3$-5-methyl-1,3,4-thiadiazole | |
| 20 | C(CH$_3$)$_3$ | 4-F-phenyl | 2-CHCl$_2$-5-methyl-1,3,4-thiadiazole | |

US 6,544,931 B1
TABLE 1-continued
Examples of compounds of the formula (I)
| Ex. No. | R | 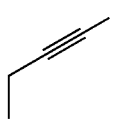 | Z | Physical data |
|---|---|---|---|---|
| 21 | 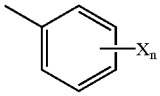 | 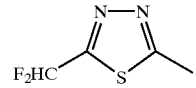 | 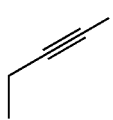 | |
| 22 | 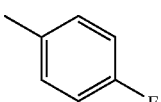 |  | 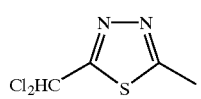 | |
| 23 | 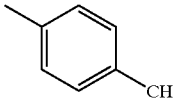 | 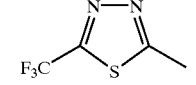 | 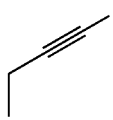 | |
| 24 | 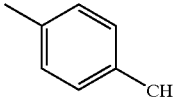 | 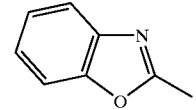 | 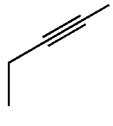 | |
| 25 | 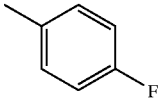 | 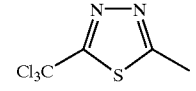 | 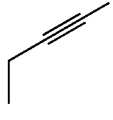 | |
| 26 | 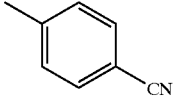 | 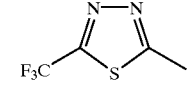 | 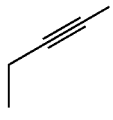 | |
| 27 | 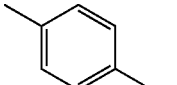 | 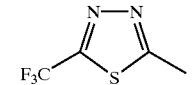 |  | |
| 28 | C(CH$_3$)$_3$ | 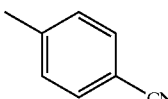 | 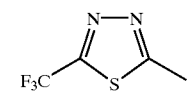 | |
| 29 | C(CH$_3$)$_3$ |  | 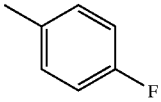 | |
| 30 | C(CH$_3$)$_3$ | 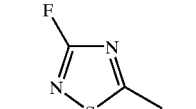 | 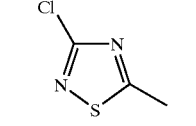 | logP = 3.60[a] |

US 6,544,931 B1

TABLE 1-continued

Examples of compounds of the formula (I)

| Ex. No. | R | (aryl with $X_n$) | Z | Physical data |
|---|---|---|---|---|
| 31 | 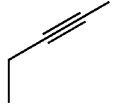 | 4-F-phenyl | 3-F-5-methyl-1,2,4-thiadiazole | |
| 32 | 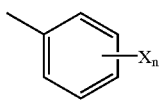 | 4-F-phenyl | 3-Cl-5-methyl-1,2,4-thiadiazole | |
| 33 | 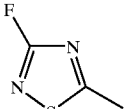 | 4-Cl-phenyl | 2-CF$_3$-5-methyl-1,3,4-thiadiazole | |
| 34 | 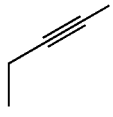 | phenyl | 2-CF$_3$-5-methyl-1,3,4-thiadiazole | |
| 35 | 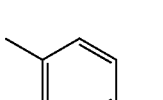 | 3-Cl-phenyl | 2-CF$_3$-5-methyl-1,3,4-thiadiazole | |
| 36 | 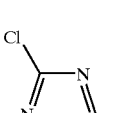 | 4-CH$_3$-phenyl | 6-Cl-2-methylbenzoxazole | |
| 37 | C(CH$_3$)$_3$ | 4-CH$_3$-phenyl | 6-Cl-2-methylbenzoxazole | |
| 38 | C(CH$_3$)$_3$ | 4-CH$_3$-phenyl | 2-methylbenzoxazole | |
| 39 | 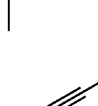 | 2-F-phenyl | 2-CF$_3$-5-methyl-1,3,4-thiadiazole | |
| 40 | 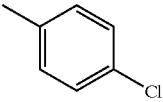 | 2-Cl-phenyl | 2-CF$_3$-5-methyl-1,3,4-thiadiazole | |

TABLE 1-continued
Examples of compounds of the formula (I)
| Ex. No. | R | (aryl) | Z | Physical data |
|---|---|---|---|---|
| 41 | 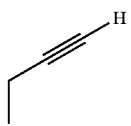 | 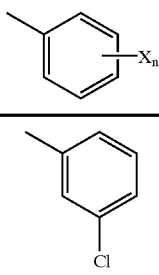 | 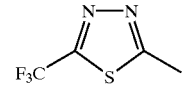 | |
| 42 | 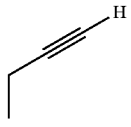 | 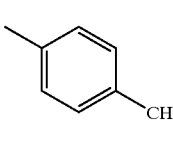 | 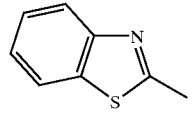 | |
| 43 | C(CH$_3$)$_3$ | 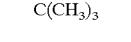 | 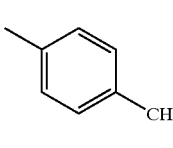 | |
| 44 | 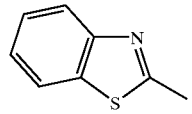 | 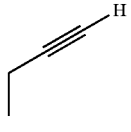 | 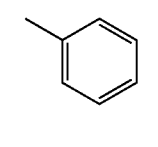 | |
| 45 | C(CH$_3$)$_3$ | 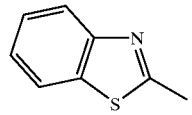 | 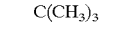 | |
| 46 | C(CH$_3$)$_3$ | 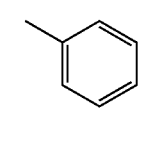 | 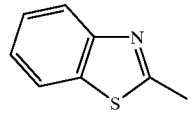 | |
| 47 | C(CH$_3$)$_3$ |  | 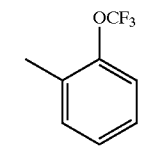 | |
| 48 | C(CH$_3$)$_3$ | 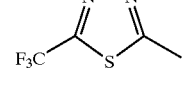 | 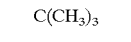 | |
| 49 | C(CH$_3$)$_3$ | 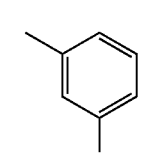 | 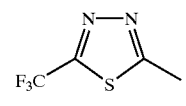 | logP = 3.65[a)] |
| 50 | C(CH$_3$)$_3$ |  | 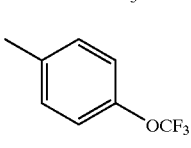 | logP = 3.53[a)] |

TABLE 1-continued

Examples of compounds of the formula (I)

| Ex. No. | R | (aryl-Xn) | Z | Physical data |
|---|---|---|---|---|
| 51 | C(CH₃)₃ | 4-F-phenyl | 3-isopropyl-5-methyl-1,2,4-thiadiazole | logP = 4.05[a] |
| 52 | C(CH₃)₃ | 4-F-phenyl | 2-(chlorodifluoromethyl)-5-methyl-1,3,4-thiadiazole | logP = 3.95[a] |
| 53 | C(CH₃)₃ | 4-F-phenyl | 7-chloro-2-methylbenzothiazole | logP = 4.83[a] |
| 54 | C(CH₃)₃ | 4-F-phenyl | 5-methyl-7-nitro-2-methylbenzothiazole | logP = 4.59[a] |
| 55 | C(CH₃)₃ | 4-F-phenyl | 3-chloro-5-methyl-1,2,4-oxadiazole | logP = 3.51[a] |
| 56 | C(CH₃)₃ | 4-Cl-phenyl | 3-methylthio-5-methyl-1,2,4-thiadiazole | logP = 4.22[a] |
| 57 | C(CH₃)₃ | 4-Cl-phenyl | 3-bromo-5-methyl-1,2,4-thiadiazole | logP = 4.09[a] |
| 58 | C(CH₃)₃ | 4-Cl-phenyl | 4-chloro-5-nitro-2-methylthiazole | logP = 4.35[a] |
| 59 | C(CH₃)₃ | 4-Cl-phenyl | 3-ethyl-5-methyl-1,2,4-thiadiazole | logP = 4.01[a] |

TABLE 1-continued

Examples of compounds of the formula (I)

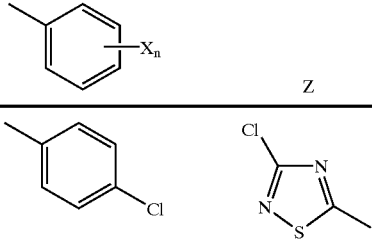

| Ex. No. | R | | Z | Physical data |
|---|---|---|---|---|
| 60 | C(CH$_3$)$_3$ | 4-Cl-C$_6$H$_4$ | 3-Cl-5-methyl-1,2,4-thiadiazol-2-yl | logP = 4.04[a)] |
| 61 | C(CH$_3$)$_3$ | 4-Cl-C$_6$H$_4$ | 7-Cl-2-methylbenzothiazol-yl | logP = 5.32[a)] |
| 62 | C(CH$_3$)$_3$ | 4-Cl-C$_6$H$_4$ | 5-methyl-7-nitro-2-methylbenzothiazol-yl | logP = 5.05[a)] |
| 63 | C(CH$_3$)$_3$ | 4-Cl-C$_6$H$_4$ | 3-Cl-5-methyl-1,2,4-oxadiazol-2-yl | logP = 3.91[a)] |
| 64 | CH(C$_2$H$_5$)$_2$ | 4-F-C$_6$H$_4$ | 5-trifluoromethyl-2-methyl-1,3,4-thiadiazol-yl | m.p.: 72° C. |

The lopP values given in Table 1 were determined in accordance with EEC directive 79/831 Annex V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient of 10% acetonitrile to 90% acetonitrile—corresponding data in Table 1 are labelled a).

(b) Mobile phases for the determination in the neutral range: 0.01 molar aqueous phosphate buffer solution, acetonitrile; linear gradient from 10% acetonitrile to 90% acetonitrile—corresponding data in Table 1 are labelled b).

Calibration was carried out using unbranched alkan-2-ones (with 3 to 16 carbon atoms) whose logP values are known (determination of the logP values by the retention times using linear interpolation between two successive alkanones).

The lambda max values were determined in the maxima of the chromatographic signals using the UV spectra from 200 nm to 400 nm.

Starting Materials of the Formula (III)

Example (III-1)

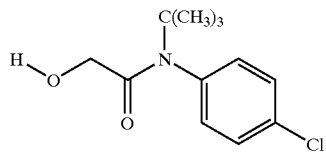

A mixture of 22 g (85 mmol) of N-(t-butyl)-N-(4-chlorophenyl)-2-chloro-acetamide, 3.3 g of potassium carbonate and 0.3 g of triethylamine is heated to 120° C., and 10.5 g of sodium acetate are added with stirring and a little at a time to this mixture, over a period of 2 hours. The mixture is then stirred at 120° C. for another 2 hours and subsequently cooled to 50° C. 200 ml of methanol are added, and the mixture is then heated under reflux for 4 hours. After concentration under waterpump vacuum, the residue is shaken with 300 ml of water/300 ml of methylene chloride and the organic phase is separated off, washed with water, IN hydrochloric acid and then once more with water, dried with sodium sulphate and filtered. From the filtrate, the solvent is carefully distilled off under reduced pressure.

This gives 20.8 g (100% of theory) of N-(t-butyl)-N-(4-chlorophenyl)-2-hydroxyacetamide.

logP (at pH=2.3): 2.54.

Example (III-2)

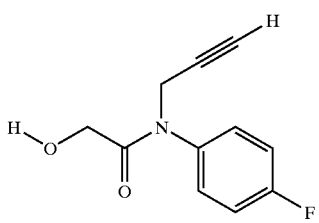

A mixture of 20 g (80 mmol) of N-(4-fluorophenyl)-N-(2-propinyl)-2-acetoxy-acetamide, 0.22 g (4 mmol) of potassium hydroxide and 200 ml of methanol is heated under reflux for 4 hours and then concentrated under water-pump vacuum. The residue is shaken with methylene chloride/water and the organic phase is separated off, dried with sodium sulphate and filtered. From the filtrate, the solvent is carefully distilled off under reduced pressure.

This gives 14.9 g (90% of theory) of N-(4-fluorophenyl)-N-(2-propinyl)-2-hydroxyacetamide of melting point 57° C.

Analogously to Examples (111-1) and (111-2), it is also possible to prepare, for example, the compounds of the general formula (III) listed in Table 2 below.

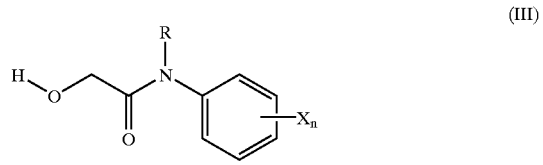

TABLE 2

Examples of compounds of the formula (III)

| Ex. No. | R | Aryl | Physical data |
|---|---|---|---|
| III-3 | CH₃-CH₂-C≡C-H | 3-CF₃-phenyl | logP = 1.89[a] |
| III-4 | C(CH₃)₃ | 2-Cl-phenyl | logP = 2.40[a] |
| III-5 | C(CH₃)₃ | phenyl | logP = 2.10[a] |
| III-6 | CH₃-CH₂-C≡C-H | 4-Cl-phenyl | |
| III-7 | CH₃-CH₂-C≡C-H | phenyl | |
| III-8 | CH₃-C≡C-H | 2-F-phenyl | |
| III-9 | CH₃-CH₂-C≡C-H | 4-CH₃-phenyl | |
| III-10 | C(CH₃)₃ | 4-CH₃-phenyl | |
| III-11 | C(CH₃)₃ | 3-CH₃-phenyl | |
| III-12 | C(CH₃)₃ | 3-F-phenyl | logP = 2.15[a] |
| III-13 | C(CH₃)₃ | 2-F-phenyl | logP = 2.17[a] |
| III-14 | C(CH₃)₃ | 3-Cl-phenyl | logP = 2.49[a] |
| III-15 | C(CH₃)₃ | 4-F-phenyl | |

TABLE 2-continued

Examples of compounds of the formula (III)

| Ex. No. | R | (aryl) | Physical data |
|---|---|---|---|
| III-16 | C(CH$_3$)$_3$ | 3-CF$_3$-phenyl | m.p.: 57° C. |
| III-17 | C(CH$_3$)$_3$ | 2-OCF$_3$-phenyl | m.p.: 103° C. |
| III-18 | C(CH$_3$)$_3$ | 4-OCF$_3$-phenyl | m.p.: 91° C. |
| III-19 | CH(C$_2$H$_5$)$_2$ | 4-F-phenyl | |

Intermediates of the Formula (V)

Example (V-1)

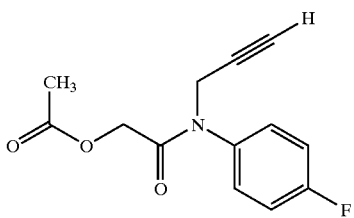

A mixture of 20 g (88.5 mmol) of N-(4-fluorophenyl)-N-(2-propinyl)-2-chloro-acetamide, 8.7 g (106 mmol) of sodium acetate, 1 g of benzyltriethylammonium chloride and 200 ml of toluene is heated under reflux for 7 hours. After cooling to room temperature, the mixture is washed with 1N hydrochloric acid and then with water, dried with sodium sulphate and filtered. From the filtrate, the solvent is carefully distilled off under reduced pressure.

This gives 21.3 g (96% of theory) of N-(4-fluorophenyl)-N-(2-propinyl)-2-acetoxy-acetamide.

Analogously to Example (V-1), it is also possible to prepare, for example, the compounds of the general formula (V) listed in Table 3 below.

TABLE 3

Examples of compounds of the formula (V)

| Ex. No. | R | (aryl) | Physical data |
|---|---|---|---|
| V-2 | CH$_2$C≡CH (butynyl) | 3-CF$_3$-phenyl | logP = 2.42[a] |
| V-3 | butynyl | 3-Cl-phenyl | |
| V-4 | C(CH$_3$)$_3$ | 2-Cl-phenyl | |
| V-5 | C(CH$_3$)$_3$ | phenyl | |
| V-6 | butynyl | 4-Cl-phenyl | |
| V-7 | butynyl | phenyl | |
| V-8 | butynyl | 2-F-phenyl | |
| V-9 | butynyl | 4-CH$_3$-phenyl | |

TABLE 3-continued

Examples of compounds of the formula (V)

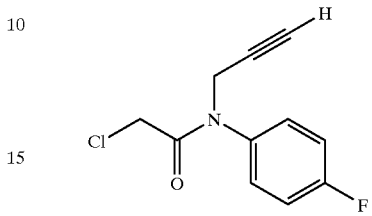

| Ex. No. | R | | Physical data |
|---|---|---|---|
| V-10 | C(CH$_3$)$_3$ | 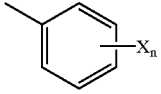 | |
| V-11 | C(CH$_3$)$_3$ | 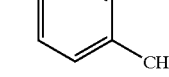 | |
| V-12 | C(CH$_3$)$_3$ | 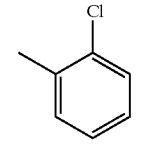 | |
| V-13 | C(CH$_3$)$_3$ | 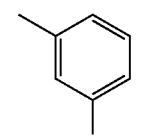 | |
| V-14 | C(CH$_3$)$_3$ | 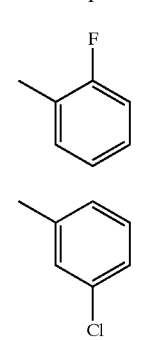 | |
| V-15 | C(CH$_3$)$_3$ | 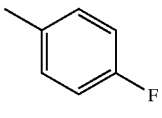 | |
| V-16 | CH(C$_2$H$_5$)$_2$ | 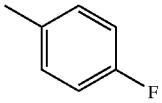 | |

Precursors of the Formula (IV)

Example (IV-1)

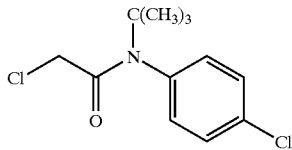

A mixture of 18.4 g (100 mmol) of N-(t-butyl)-N-(4-chlorophenyl)-amine, 6.2 g (55 mmol) of chloroacetyl chloride and 50 ml of toluene is heated under reflux until a clear solution has formed. A further 6.2 g (55 mmol) of chloroacetyl chloride are then added, and the mixture is heated under reflux until evolution of gas (HCl) has ceased. The mixture is then concentrated under waterpump vacuum and the residue is distilled under reduced pressure.

This gives 22 g (89% of theory) of N-(t-butyl)-N-(4-chlorophenyl)-2-chloroacetamide.

logP (at pH=2.5): 3.34.

Example (IV-2)

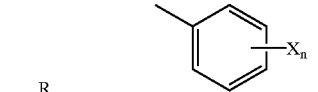

At room temperature (about 20° C.), a solution of 11.3 g (0.1 mol) of chloroacetyl chloride in 30 ml of toluene is added dropwise with stirring to a mixture of 15 g (0.1 mol) of N-(4-fluorophenyl)-N-(2-propinyl)-amine, 8.4 g of pyridine and 200 ml of toluene, and the reaction mixture is stirred at room temperature for 15 hours. The mixture is then washed with saturated aqueous sodium chloride solution and with water, dried with sodium sulphate and filtered. The filtrate is concentrated under waterpump vacuum, the residue is digested with diisopropyl ether and the resulting crystalline product is isolated by filtration with suction.

This gives 20.5 g (90% of theory) of N-(4-fluorophenyl)-N-(2-propinyl)-2-chloroacetamide of melting point 115° C.

Analogously to Examples (IV-1) and (IV-2), it is also possible to prepare, for example, the compounds of the general formula (I) listed in Table 4 below.

(IV)

TABLE 4

Examples of the compounds of the formula (IV)
X$^2$ represents in each case Cl

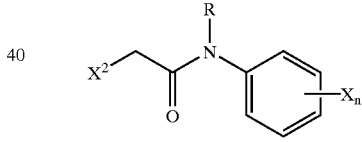

| Ex. No. | R | | Physical data |
|---|---|---|---|
| IV-2 | H | CF$_3$ | logP = 2.69[a)] |
| IV-3 | H | Cl | |

TABLE 4-continued
Examples of the compounds of the formula (IV)
X² represents in each case Cl
| Ex. No. | R | | Physical data |
|---|---|---|---|
| IV-4 | C(CH₃)₃ | 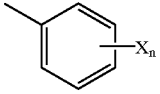 | logP = 3.19[a] |
| IV-5 | C(CH₃)₃ | 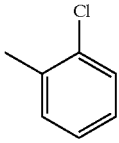 | logP = 2.83[a] |
| IV-6 | 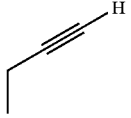 | 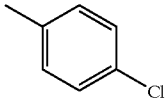 | |
| IV-7 | 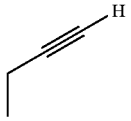 | 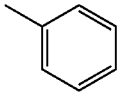 | |
| IV-8 |  | 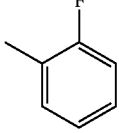 | |
| IV-9 |  | 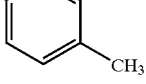 | |
| IV-10 | C(CH₃)₃ | 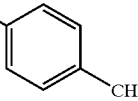 | |
| IV-11 | C(CH₃)₃ | 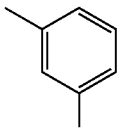 | |
| IV-12 | C(CH₃)₃ | 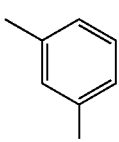 | |
TABLE 4-continued
Examples of the compounds of the formula (IV)
X² represents in each case Cl
| Ex. No. | R | | Physical data |
|---|---|---|---|
| IV-13 | C(CH₃)₃ | 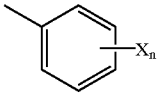 | logP = 2.92[a] |
| IV-14 | C(CH₃)₃ | 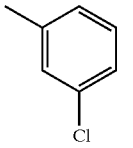 | logP = 3.27[a] |
| IV-15 | C(CH₃)₃ | 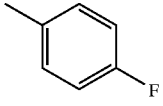 | |
| IV-16 | 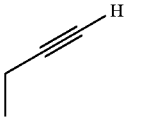 | 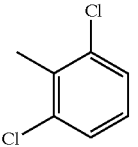 | |
| IV-17 | 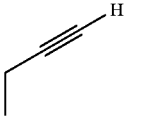 | 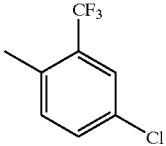 | |
| IV-18 | 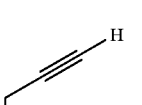 | 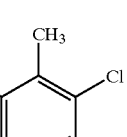 | |
| IV-19 | 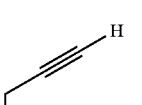 | 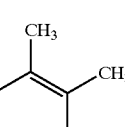 | |

TABLE 4-continued

Examples of the compounds of the formula (IV)
$X^2$ represents in each case Cl

| Ex. No. | R | Aryl (with $X_n$) | Physical data |
|---|---|---|---|
| IV-20 | CH≡C–CH₂– (propargyl, H terminal) | 2,4-dimethyl-... wait |

| Ex. No. | R | Ar–$X_n$ substitution | Physical data |
|---|---|---|---|
| IV-20 | –C≡C–CH₂CH₃ (but-2-ynyl, H on alkyne) | 2-CH₃, 4-Cl, (with ring-CH₃) | |
| IV-21 | –C≡C–CH₂CH₃ | 2,3-(CH₃)₂ | |
| IV-22 | –C≡C–CH₂CH₃ | 2-CH₃ | |
| IV-23 | –C≡C–CH₂CH₃ | 2-CH₃, 3-Cl | |
| IV-24 | –C≡C–CH₂CH₃ | 3-CH₃ | |
| IV-25 | C(CH₃)₃ | 3-CF₃ | |
| IV-26 | C(CH₃)₃ | 2-OCF₃ | |
| IV-27 | C(CH₃)₃ | 4-OCF₃ | |
| IV-28 | CH(C₂H₅)₂ | 4-F | |

Use Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litre of water per hectare.

After three weeks, the degree of damage to the plants is rated in % damage in comparison to the development of the untreated controls.

The figures denote:

0%=no effect (like untreated control)
100%=total destruction

In this test, for example, the compounds of Preparation Examples 1, 3, 4, 6, 7, 9 and 11 show strong activity against weeds, and some of them are tolerated well by crop plants, such as, for example, cotton, maize, wheat and sugar beet.

TABLE A1

Pre-emergence test/greenhouse

| Active compound according to Preparation Example No. | Application rate (g of ai/ha) | Maize | Cotton | Eriochloa | Lolium | Setaria | Amaranthus |
|---|---|---|---|---|---|---|---|
| (3) | 500 | 0 | 0 | 95 | 100 | 100 | 100 |

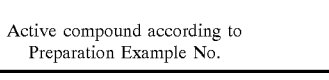

TABLE A2

Pre-emergence test/greenhouse

| Active compound according to Preparation Example No. | Application rate (g of ai/ha) | Maize | Setaria | Amaranthus | Matricaria | Veronica |
|---|---|---|---|---|---|---|
| (4) | 125 | 0 | 100 | 100 | 100 | 100 |

TABLE A3

Pre-emergence test/greenhouse

| Active compound according to Preparation Example No. | Application rate (g of ai/ha) | Setaria | Amaranthus | Sinapis |
|---|---|---|---|---|
| (6) | 500 | 100 | 100 | 95 |

TABLE A4

| | Pre-emergence test/greenhouse | | | | | | |
|---|---|---|---|---|---|---|---|
| Active compound according to Preparation Example No. | Application rate (g of ai/ha) | Wheat | Alope-curus | Digitaria | Erio-chloa | Setaria | Ama-ranthus |
| 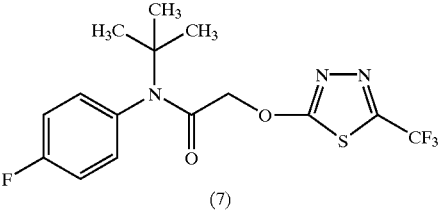 (7) | 500 | 0 | 90 | 100 | 100 | 100 | 95 |

TABLE A5

| | Pre-emergence test/greenhouse | | | | | |
|---|---|---|---|---|---|---|
| Active compound according to Preparation Example No. | Application rate (g of ai/ha) | Maize | Alopecurus | *Avena fatua* | Echinochloa | Setaria |
| 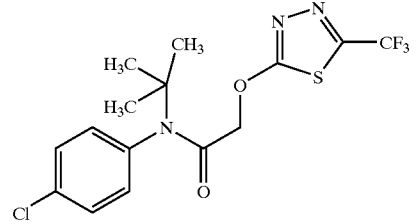 (1) | 500 | 0 | 80 | 80 | 95 | 100 |

TABLE A6

| | Pre-emergence test/greenhouse | | | | | |
|---|---|---|---|---|---|---|
| Active compound according to Preparation Example No. | Application rate (g of ai/ha) | Maize | Sugar beet | Alopecurus | Echinochloa | Setaria |
| 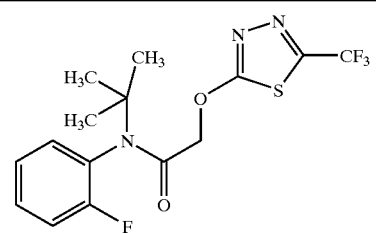 (11) | 500 | 0 | 0 | 80 | 95 | 90 |

TABLE A7

Pre-emergence test/greenhouse

| Active compound according to Preparation Example No. | Application rate (g of ai/ha) | Maize | Sugar beet | Echinochloa | Setaria |
|---|---|---|---|---|---|
| 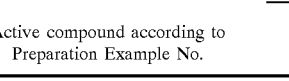 (9) | 500 | 0 | 0 | 95 | 100 |

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5 to 15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 1, 2, 3, 4, 6, 7 and 9 show strong activity against weeds.

TABLE B1

Post-emergence test/greenhouse

| Active compound according to Preparation Example No. | Application rate (g of ai/ha) | Setaria | Amaranthus | Galium | Sinapis |
|---|---|---|---|---|---|
| 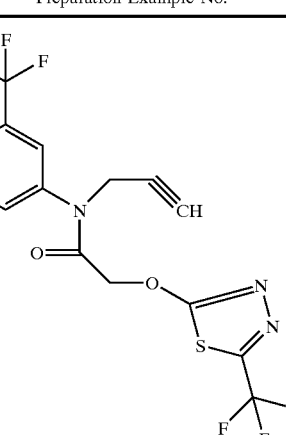 (3) | 2000 | 95 | 100 | 90 | 100 |
| 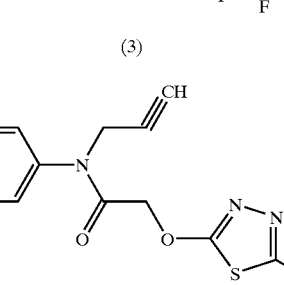 (4) | 2000 | 90 | 95 | 90 | 95 |

TABLE B1-continued
Post-emergence test/greenhouse
| Active compound according to Preparation Example No. | Application rate (g of ai/ha) | Setaria | Amaranthus | Galium | Sinapis |
|---|---|---|---|---|---|
| 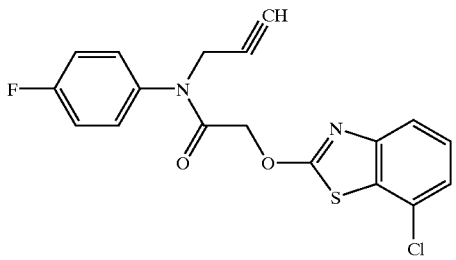 (2) | 2000 | 90 | 90 | — | 90 |
| 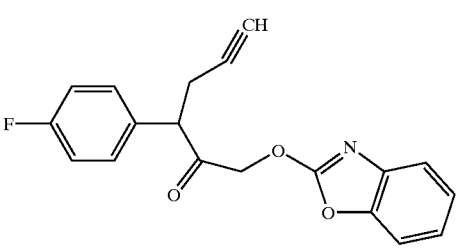 (6) | 500 | 90 | 90 | 90 | — |
| 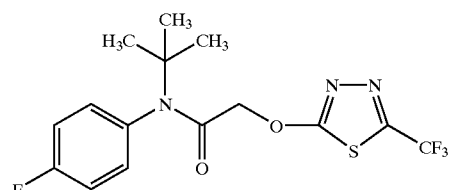 (7) | 1000 | 80 | 80 | 95 | 80 |
TABLE B2
Post-emergence test/greenhouse
| Active compound according to Preparation Example No. | Application rate (g of ai/ha) | *Avena fatua* | Setaria | Galium | Ipomoea |
|---|---|---|---|---|---|
| 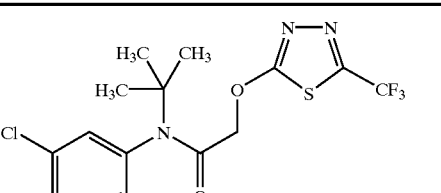 (9) | 500 | — | 70 | 90 | 90 |

TABLE B2-continued

| Structure | | | | | |
|---|---|---|---|---|---|
| (Compound with 4-chlorophenyl, N-t-butyl-like group, acetamide linker, O-CH2, and 5-(trifluoromethyl)-1,3,4-thiadiazol-2-yl) (1) | 500 | 80 | 90 | 90 | 90 |

What is claimed is:

1. A compound of the formula (I), (I)

[Structure: Z-O-CH2-C(=O)-N(R)-phenyl-X_n]

wherein n represents the number 0, 1, 2 or 3,

R represents t-butyl, 1-ethyl-propyl or 2-propynyl,

X represents nitro, cyano, fluorine, chlorine, bromine or represents optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, and Z represents a heteroaryl selected from the group consisting of oxazolyl, benzoxazolyl, benzothiazolyl, oxadiazolyl, thiadiazolyl, which is optionally substituted by nitro, cyano, carbamoyl, thiocarbamoyl, fluorine, chlorine, bromine, or by optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl.

2. The compound of claim 1, wherein n represents the number 0, 1 or 2,

R represents t-butyl, 1-ethyl-propyl or 2-propynyl,

X represents nitro, cyano, fluorine, chlorine, bromine or represents optionally cyano-, fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl or ethylsulphonyl, and Z represents a heteroaryl selected from the group consisting of oxazolyl, benzoxazolyl, benzothiazolyl, 1,2,4-oxadiazolyl, 1,3,4-oxadiazolyl, 1,2,4-thiadiazolyl, 1,3,4-thiadiazolyl, which is optionally substituted by nitro, cyano, carbamoyl, thiocarbamoyl, fluorine, chlorine, bromine, or by optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

3. The compound of claim 1 wherein n represents the number 0, 1 or 2,

R represents t-butyl, 1-ethyl-propyl or 2-propynyl,

X represents nitro, cyano, fluorine, chlorine, bromine or represents optionally fluorine- and/or chlorine-substituted methyl, ethyl, n- or i-propyl, methoxy, ethoxy, methylthio, ethylthio, methylsulphinyl, ethylsulphinyl, methylsulphonyl or ethylsulphonyl, and Z represents a heteroaryl selected from the group consisting of oxazolyl, benzoxazolyl, benzothiazolyl, 1,2,4-oxadiazolyl, 1,2,4-thiadiazolyl, 1,3,4-thiadiazolyl, which is optionally substituted by nitro, cyano, carbamoyl, thiocarbamoyl, fluorine, chlorine, bromine, or by optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl.

4. The compound of claim 1 wherein n represents the number 0 or 1,

R represents t-butyl, 1-ethyl-propyl or 2-propynyl,

X represents cyano, fluorine, chlorine, methyl, ethyl, trifluoromethyl, methoxy or trifluoromethoxy, and Z represents a heteroaryl selected from the group consisting of oxazolyl, benzoxazolyl, benzothiazolyl, 1,2,4-oxadiazolyl, 1,2,4-thiadiazolyl, 1,3,4-thiadiazolyl, which is optionally substituted by nitro, fluorine, chlorine, bromine, methyl, ethyl, n- or i-propyl, difluoromethyl, trifluoromethyl, difluorochloromethyl, fluorodichloromethyl, dichloromethyl, trichloromethyl, methylthio, ethylthio, n- or i-propylthio.

5. The compound of claim 1 wherein n represents the number 0 or 1,

R represents t-butyl, 1-ethyl-propyl or represents 2-propynyl,

X represents cyano, fluorine, chlorine, methyl, ethyl, trifluoromethyl, methoxy or trifluoromethoxy, and Z represents a heteroaryl selected from the group consisting of oxazolyl, benzoxazolyl, benzothiazolyl, 1,2,4-oxadiazolyl, 1,2,4-thiadiazolyl, 1,3,4-thiadiazolyl, which is optionally substituted by fluorine, chlorine, bromine, methyl, ethyl, n- or i-propyl, difluoromethyl, trifluoromethyl, dichloromethyl, difluorochloromethyl, fluorodichloromethyl, trichloromethyl, methylthio, ethylthio, n- or i-propylthio.

6. A process for preparing a compound of claim 1 comprising reacting a heteroarene of the formula (II)

$$Z\text{---}X^1 \quad (II)$$

wherein

Z is as defined in claim 1 and $X^1$ represents fluorine, chlorine, bromine, methylthio, methylsulphinyl or methylsulphonyl, with a hydroxyacetanilide of the formula (III)

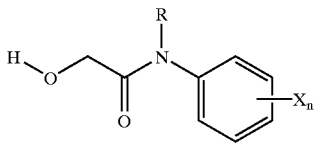

wherein
n, R and X are as defined in claim 1.

7. A method for controlling plant growth comprising applying at least one compound of claim 1 to said plant and/or its locus.

8. A herbicidal composition comprising at least one compound of claim 1 and at least one of extender and surfactant.

* * * * *